US009049992B2

(12) United States Patent
Burmeister

(10) Patent No.: US 9,049,992 B2
(45) Date of Patent: Jun. 9, 2015

(54) METHOD AND APPARATUS FOR A STETHOSCOPE

(71) Applicant: Karen G. Burmeister, North Brunswick, NJ (US)

(72) Inventor: Karen G. Burmeister, North Brunswick, NJ (US)

( * ) Notice: Subject to any disclaimer, the term of this patent is extended or adjusted under 35 U.S.C. 154(b) by 0 days.

(21) Appl. No.: 14/465,882

(22) Filed: Aug. 22, 2014

(65) Prior Publication Data

US 2015/0101881 A1   Apr. 16, 2015

Related U.S. Application Data

(63) Continuation-in-part of application No. 14/052,796, filed on Oct. 14, 2013.

(51) Int. Cl.
*A61B 7/02* (2006.01)
*A61B 19/02* (2006.01)
*A61B 7/00* (2006.01)

(52) U.S. Cl.
CPC .. *A61B 7/02* (2013.01); *A61B 19/02* (2013.01)

(58) Field of Classification Search
USPC ............. 181/131; 381/67; 600/528; 128/864
See application file for complete search history.

(56) References Cited

U.S. PATENT DOCUMENTS

| | | | | |
|---|---|---|---|---|
| 3,730,290 A | * | 5/1973 | Scanlon | 181/135 |
| 3,772,478 A | * | 11/1973 | McCabe et al. | 381/67 |
| 3,899,044 A | * | 8/1975 | Stumpf et al. | 181/135 |
| 3,934,674 A | * | 1/1976 | Shore et al. | 181/135 |
| 4,011,925 A | * | 3/1977 | French et al. | 181/131 |
| 4,029,169 A | * | 6/1977 | Huntress | 181/135 |
| 4,149,610 A | * | 4/1979 | Saiya et al. | 181/131 |
| 4,177,871 A | * | 12/1979 | Clanton | 181/131 |
| 4,282,678 A | * | 8/1981 | Tsui | 446/193 |
| 4,991,686 A | * | 2/1991 | Allen | 181/131 |
| 5,466,898 A | | 11/1995 | Gilbert et al. | |
| 5,486,659 A | | 1/1996 | Rosenbush | |
| 5,539,162 A | | 7/1996 | Tuttle | |
| D376,043 S | | 12/1996 | Rix | |
| 5,592,946 A | | 1/1997 | Eddy | |
| 5,623,131 A | | 4/1997 | Earnest | |
| 5,663,533 A | * | 9/1997 | Judge | 181/141 |
| 6,006,856 A | | 12/1999 | Skubal et al. | |
| 6,165,035 A | | 12/2000 | Avner | |
| 6,186,957 B1 | | 2/2001 | Milam | |
| D455,254 S | | 4/2002 | Sanchez-Thomas | |
| 6,520,639 B2 | | 2/2003 | Avner | |
| 6,575,917 B2 | | 6/2003 | Giroux et al. | |
| 6,966,400 B1 | | 11/2005 | Rollins et al. | |
| 7,296,652 B1 | | 11/2007 | Rosenberg | |
| 7,314,112 B1 | | 1/2008 | Rollins et al. | |
| 7,614,477 B2 | | 11/2009 | Statner et al. | |
| 7,712,575 B1 | | 5/2010 | Moore | |
| 7,806,267 B2 | | 10/2010 | Pack-Walden et al. | |

(Continued)

*Primary Examiner* — Edgardo San Martin
(74) *Attorney, Agent, or Firm* — Walter J. Tencza, Jr.

(57) ABSTRACT

A covering device having first, second, and third bores in which first, second, and third portions of tubing, respectively, of a stethoscope can be inserted when the covering device is attached to the stethoscope in a first state. Each of the first, second, and third bores may have a length and a width, wherein the length of each of the first, second, and third bores is greater than its width, and wherein the width of each of the first, second and third bores is less than the outer diameter of a diaphragm device of the stethoscope. The covering device may have first, second, and third slits, each of which can be pried open to allow the first, second, and third portions of tubing to be inserted into the first, second, and third bores of the covering device, respectively.

15 Claims, 13 Drawing Sheets

(56) References Cited

U.S. PATENT DOCUMENTS

| | | | |
|---|---|---|---|
| 8,025,120 B2 * | 9/2011 | Eddy | 181/131 |
| D671,210 S * | 11/2012 | Manta | D24/134 |
| 2002/0170771 A1 | 11/2002 | Milam et al. | |
| 2004/0256172 A1 | 12/2004 | Darling | |
| 2009/0165186 A1 | 7/2009 | Mijares et al. | |
| 2009/0288908 A1 | 11/2009 | Giroux et al. | |
| 2013/0341223 A1 | 12/2013 | Fong | |

* cited by examiner

METHOD AND APPARATUS FOR A STETHOSCOPE

CROSS REFERENCE TO RELATED APPLICATION(S)

The present application is a continuation in part of and claims the priority of U.S. patent application Ser. No. 14/052,796, filed on Oct. 14, 2013, inventor and applicant Karen G. Burmeister.

FIELD OF THE INVENTION

This invention relates to improved methods and apparatus concerning stethoscopes.

BACKGROUND OF THE INVENTION

Many medical professionals spend anywhere from eighty dollars to two hundred dollars on a good stethoscope only to have the tubing get hard and crack after a year or two of using it. Stethoscopes are frequently worn slung around a person's neck, when they are not being used to examine a patient, and this causes the tubing to be against the person's skin. Acids in the perspiration from the person's skin break down the plastic tubing causing it to get hard and crack. Fabric covers have been used to cover the tubing, but when an individual perspired enough, the perspiration would go through the fabric and harden the stethoscope tubing and cause cracking.

In addition, fabric covers for stethoscope tubing are no longer in use because studies were done and the fabric covers were proven to harbor germs. Generally speaking, stethoscopes are disinfected after each use by using disinfecting disposable wipes or rubbing alcohol. Fabric covers cannot or cannot be easily disinfected after each use, and therefore are no longer used. At this time most medical facilities ban fabric stethoscope covers. It is also known to use flexible plastic bag type disposable covers.

SUMMARY OF THE INVENTION

At least one embodiment of the present invention provides an apparatus comprising a stethoscope including stethoscope tubing, and a device for covering the stethoscope tubing. The device for covering the stethoscope tubing may be made of a flexible and elastic material. The device for covering the stethoscope tubing may have a water proof outer shell. The water proof outer shell of the device for covering the stethoscope tubing may be made of polyurethane, silicone, or other flexible water proof coating. The device for covering the stethoscope tubing may have U-shaped portion, and a straight portion connected to a bottom of the U-shaped portion.

The device for covering the stethoscope tubing may be comprised of a first device and a second device. The first device and the second device may be configured to be attached together with the stethoscope tubing in between the first device and the second device and thereby covered by a combination of the first device and the second device. The apparatus may include a plurality of fasteners which attach the first device and the second device together.

At least one embodiment of the present invention may include a method comprising covering stethoscope tubing of a stethoscope with a device for covering the stethoscope tubing. The device for covering the stethoscope tubing may be as previously described. The step of covering the stethoscope tubing of the stethoscope preferably includes covering all of the stethoscope tubing of the stethoscope. In at least one embodiment, it is critical that all of the stethoscope tubing or substantially all is covered to avoid any moisture contacting outer surfaces of the stethoscope tubing to prevent hardening and cracking of the stethoscope tubing.

In at least one embodiment of the present invention an apparatus is provided comprising a stethoscope which includes a first ear tip device, a first portion of tubing, a second ear tip device, a second portion of tubing, a third portion of tubing, a junction portion of tubing, and a diaphragm device. The first ear tip device is connected to the first portion of tubing, the second ear tip device is connected to the second portion of tubing, the junction portion of tubing connects the first portion of tubing, the second portion of tubing, and the third portion of tubing, and the third portion of tubing is connected to the diaphragm device. The diaphragm device has an outer diameter.

In an least one embodiment, the apparatus is further comprised of a covering device for covering at least part of the first, the second, and the third portions of tubing, and the junction portion of tubing; wherein the covering device has first, second, and third bores in which the first, second, and third portions of tubing, respectively, of the stethoscope are located when the covering device is attached to the stethoscope in a first state. Each of the first, second, and third bores may have a length and a width, wherein the length of each of the first, second, and third bores is greater than its width, and wherein the width of each of the first, second and third bores is less than the outer diameter of the diaphragm device.

The first, second, and third portions of tubing of the stethoscope may be substantially parallel to the lengths of the first, second, and third bores, respectively, when the covering device is attached to the stethoscope in the first state. The covering device may be made of a flexible and elastic material. The covering device may have first, second, and third slits, each of which can be pried open to allow the first, second, and third portions of tubing to be inserted into the first, second, and third bores of the covering device, respectively. The covering device may have a water proof outer shell. The water proof outer shell of the covering device may be made of polyurethane.

The covering device may have a U-shaped portion, and a straight portion connected to a bottom of the U-shaped portion. The covering device may be configured so that the first, second, and third slits close after the first, second, and third portions or tubing, are inserted into the first, second, and third bores.

In at least one embodiment an apparatus is provided comprising a covering device for covering at least part of first, second, and third portions of tubing, and a junction portion of tubing of a stethoscope, the stethoscope including a diaphragm device connected to the third portion of tubing of the stethoscope; wherein the covering device has first, second, and third bores configured to receive first, second, and third portions of tubing, respectively, of the stethoscope when the covering device is attached to the stethoscope in a first state. Each of the first, second, and third bores may have a length and a width, wherein the length of each of the first, second, and third bores is greater than its width, and wherein the width of each of the first, second and third bores is less than an outer diameter of the diaphragm device of the stethoscope.

The first, second, and third portions of tubing of the stethoscope may be substantially parallel to the lengths of the first, second, and third bores, respectively, when the covering device is attached to the stethoscope in the first state. The covering device may have a first, second, and third slits, each of which can be pried open to allow the first, second, and third portions of tubing to be inserted into the first, second, and third bores of the covering device, respectively. The covering device may have a water proof outer shell, made of polyurethane and/or may have a U-shaped portion, and a straight portion connected to a bottom of the U-shaped portion. The covering device may be configured so that the first, second, and third slits close after the first, second, and third portions or tubing, are inserted into the first, second, and third bores.

In at least one embodiment a method is provided comprising covering stethoscope tubing, including at least a first, second, third, and junction portions of tubing of a stethoscope with a covering device by attaching the covering device to the stethoscope in a first state. The stethoscope and the covering device may be as previously described.

DETAILED DESCRIPTION OF THE DRAWINGS

Figure 1:
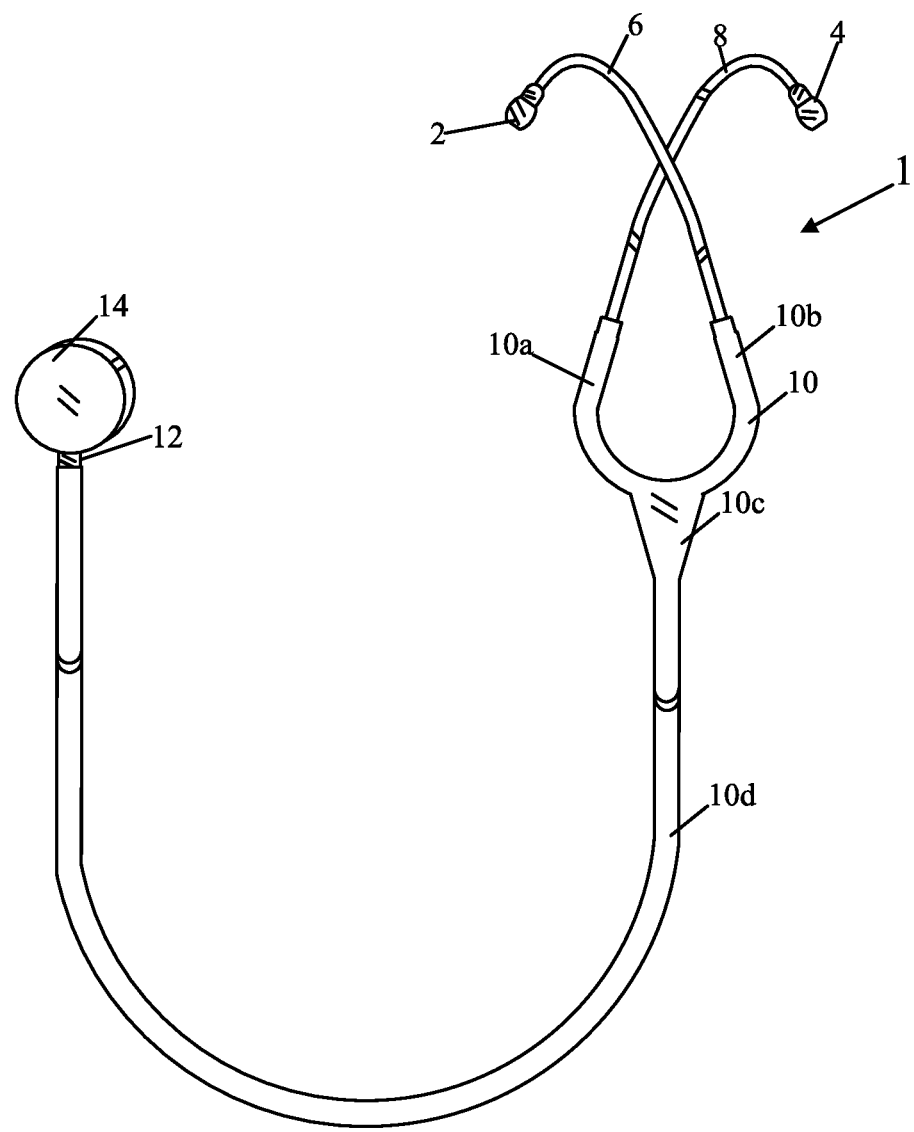
FIG. 1 shows a perspective view of a stethoscope of the prior art.

FIG. 1 shows a perspective view of a stethoscope 1 of the prior art. The stethoscope 1 may be any known stethoscope. The stethoscope 1 may include a diaphragm device or chestpiece 14, a stem 12, tubing 10, eartube devices 6 and 8, and eartips or eartip devices 2 and 4. The tubing 10 includes portions 10a, 10b, junction portion 10c, and portion 10d. The diaphragm device or chestpiece 14 connects to stem 12, which connects to one end of tubing 10. The tubing 10 connects to ear tube devices 6 and 8 near portions 10a and 10b respectively. The eartips or eartip devices 2 and 4 connect to eartube devices 6 and 8, respectively. The eartube devices 6 and 8 may be metal curved hollow tubes. In operation, as known in the art, the chestpiece 14 is placed on a patient's chest while at the same time the eartips 2 and 4 are placed into first and second ears of a medical doctor, physician, or nurse, in order to listen for a patient's heart beat. The vibrations of a patient's heartbeat cause the diaphragm device or chestpiece 14 to vibrate, which causes sound to be transmitted in the hollow stem 12, through the hollow tubing 10, into the hollow ear tube devices 6 and 8, into the eartips 2 and 4, and into the medical doctor's ears.

Figure 2A:
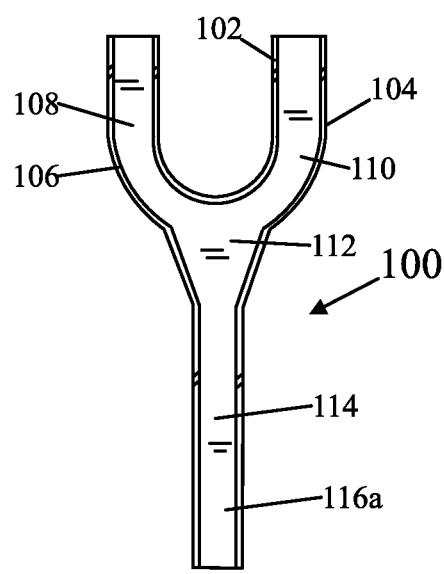
FIG. 2A shows a front view of a first device for use with the stethoscope of FIG. 1, in accordance with an embodiment of the present invention.
Figure 2C:
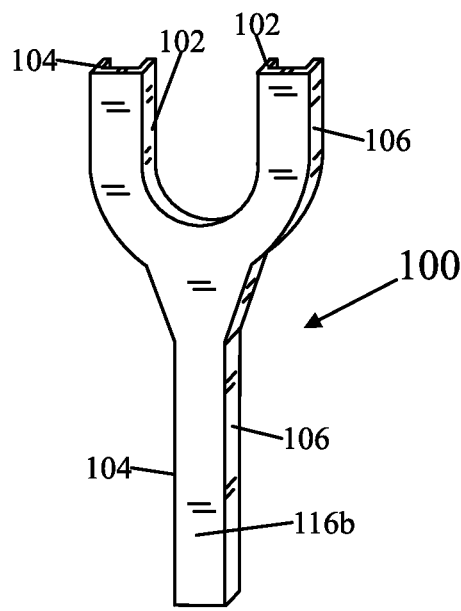
FIG. 2C shows a rear, left, top perspective view of the first device of FIG. 2A.
Figure 2B:
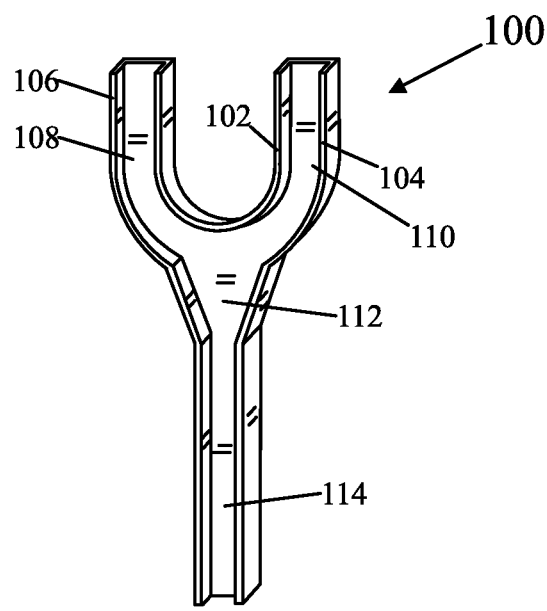
FIG. 2B shows a front, right, top perspective view of the first device of FIG. 2A.

FIG. 2A shows a front view of a first device 100 for use with the stethoscope 1 of FIG. 1, in accordance with an embodiment of the present invention. FIG. 2B shows a front, right, top perspective view of the first device 100. FIG. 2C shows a rear, left, top perspective view of the first device 100. The first device 100 includes an inner wall 102, a wall 104, and a wall 106. A channel 108 is formed between the walls 102 and 106; and a channel 110 is formed between the walls 102 and 104. The first device 100 also includes a junction 112. A channel 114 is formed between lower portions of the walls 106 and 104. The channels 108, 110, and 114 meet together at the junction 112. The device 100 has an inner surface 116a shown in FIG. 2A, and a outer surface 116b shown in FIG. 2C.

Figure 3A:
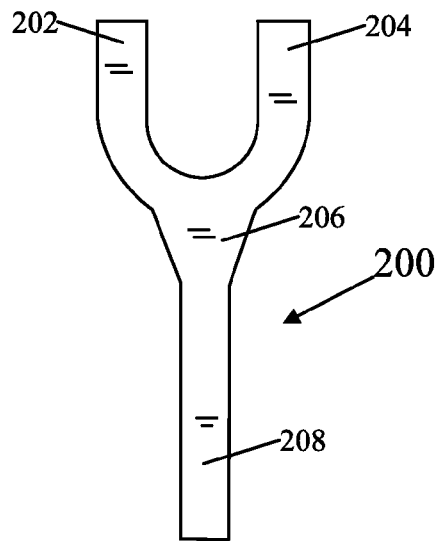
FIG. 3A shows a front view of a second device for use with the stethoscope of FIG. 1 and the first device of FIG. 2A, in accordance with an embodiment of the present invention.
Figure 3C:
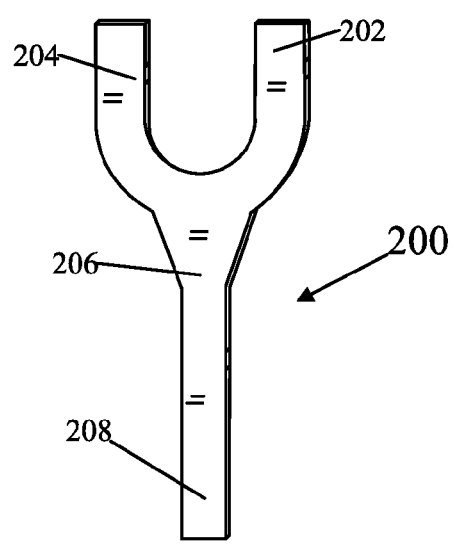
FIG. 3C shows a rear, left, top perspective view of the second device of FIG. 3A.
Figure 3B:
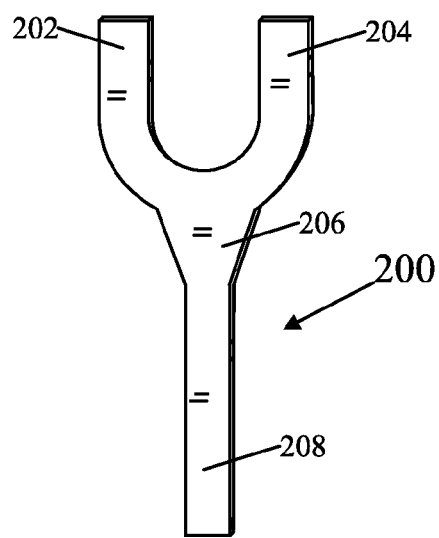
FIG. 3B shows a front, right, top perspective view of the second device of FIG. 3A.

FIG. 3A shows a front view of a second device 200 for use with the stethoscope 1 of FIG. 1 and the first device 100 of FIG. 2A, in accordance with an embodiment of the present invention. FIG. 3B shows a front, right, top perspective view of the second device 200. FIG. 3C shows a rear, left, top perspective view of the second device 200. The second device 200 may be a flat piece. The second device 200 may include a portion 202, a portion 204, a junction 206, and a portion 208. In at least one embodiment, it is critical that the second device 200 have the same outline as the first device 100 so that the second device 200 and the first device 100 can be aligned with each other and attached together as will be shown with reference to FIGS. 4B and 4C.

Figure 4A:
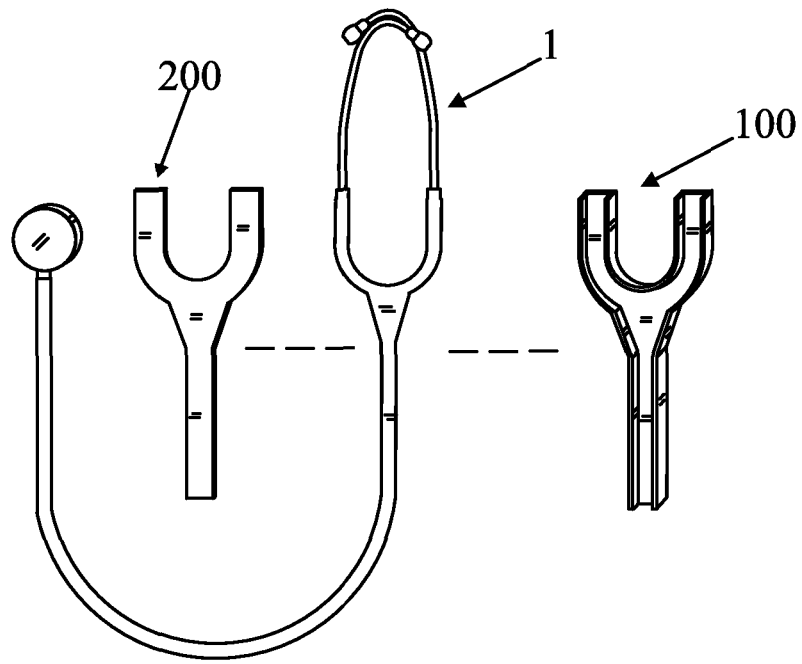
FIG. 4A shows a front, right, top perspective view of the first device of FIG. 2A, the second device of FIG. 3A, and the stethoscope of FIG. 1, with the first device, the second device, and the stethoscope shown apart from each other.
Figure 4B:
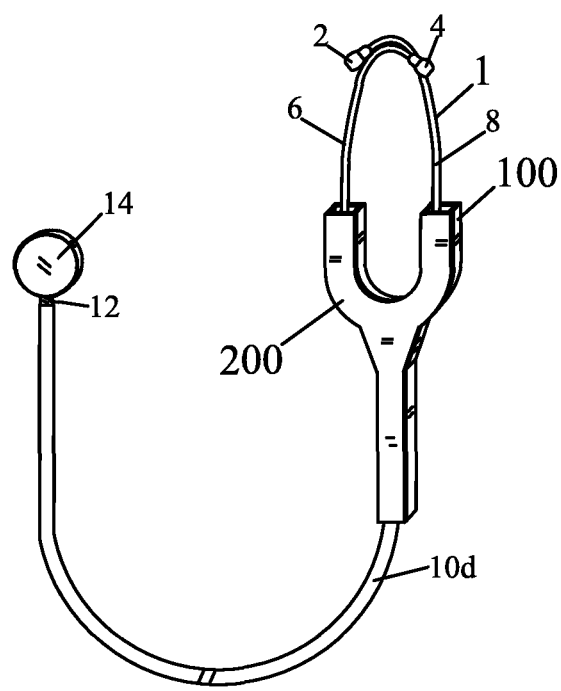
FIG. 4B shows a front, right, top perspective view of the first device of FIG. 2A, the second device of FIG. 3A, and the stethoscope of FIG. 1, with the first device, the second device, and the stethoscope shown assembled together.
Figure 4C:
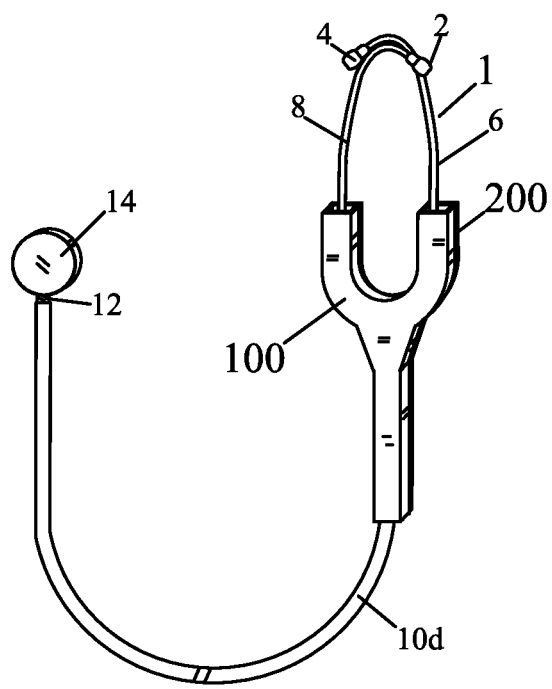
FIG. 4C shows a rear, left, top perspective view of the first device of FIG. 2A, the second device of FIG. 3A, and the stethoscope of FIG. 1, with the first device, the second device, and the stethoscope shown assembled together.

FIG. 4A shows a front, right, top perspective view of the first device 100 of FIG. 2A, the second device 200 of FIG. 3A, and the stethoscope 1 of FIG. 1, with the first device 100, the second device 200, and the stethoscope 1 shown apart from each other. FIG. 4B shows a front, right, top perspective view of the first device 100 of FIG. 2A, the second device 200 of FIG. 3A, and the stethoscope 1 of FIG. 1, with the first device 100, the second device 200, and the stethoscope 1 shown assembled together. FIG. 4C shows a rear, left, top perspective view of the first device 100, the second device 200, and the stethoscope 1, with the first device 100, the second device 200, and the stethoscope 1 shown assembled together. As shown in FIG. 4B, the first device 100 is aligned over the second device 200, and the first device 100 is attached to the second device 200, so that a portion or preferably all of the tubing 10 of the stethoscope 1 is enclosed within a combination of the first device 100 and the second device 200. In particular, the tubing portions 10a and 10b, junction 10c, and part of tubing portion 10d, are enclosed within the combination of the first device 100 and the second device 200. In FIGS. 4B and 4C, in at least one embodiment, tubing portion 10a sits within channel 108 shown in FIG. 2A, tubing portion 10b sits within channel 110 shown in FIG. 2A, junction 10c sits within channel 112 shown in FIG. 2A, and part of tubing portion 10d sits within channel 114, of the first device 100. The second device 200 then provides a cover to enclose and protect part or preferably all of tubing 10.

As known in the art, the tubing 10, in particular the tubing portions 10c and 10d, often break as a result of many uses of the stethoscope. In accordance with an embodiment of the present invention, the use of the first device 100 and the second device 200 as shown in FIGS. 4B and 4C provides a protective covering which reduces the stress on tubing 10 and prevents or inhibits the tubing 10 from hardening and breaking so that the stethoscope can be used for a longer period of time. In addition, the first device 100 and the second device 200 can be provided in various styles in order to provide a decorative aspect, and/or for use when examining children. For example the first device 100 and/or the second device 200 can be in the form of a cartoon character, or other child friendly decorative arrangement. The first device 100 and/or the second device 200 can include or have printed thereon the logos or colors of sports teams, such as professional sports teams. The first device and/or the second device can be of various colors or styles.

Each of the first device 100 and the second device 200 may be made of a flexible rubber. In at least one embodiment, it is critical that devices 100 and 200 be flexible and elastic so that after flexing of devices 100 and 200, devices 100 and 200 return to their original state. In addition, in at least one embodiment, it is critical that devices 100 and 200 be made of a material that is waterproof or has a waterproof shell or outside surface that would contact a person's skin. The first device 100 may be attached to the second device 200 by glue, by screws, or by snap fit connectors, for example the first device 100 may be attached, fixed, or otherwise connected to the second device 200 as shown in FIG. 5.

Each of the first device 100 and the second device 200 may be made of polyurethane. In at least one embodiment, the use of polyurethane is critical to keep moisture and microbes away from the portions or preferably all of the stethoscope tubing 10 covered by devices 100 and 200. The combination of the first device 100 and the second device 200 as shown in FIGS. 4B and 4C, in at least one embodiment, keep one hundred percent of the moisture and microbes away from the stethoscope tubing that they cover, such as 10a, 10b, 10c, and portions of 10d. With the first device 100 and the second device 200 put on as in FIGS. 4B and 4C, a medical practitioner no longer needs to wipe down the tubing of 10 enclosed by devices 100 and 200 with harsh chemicals. The combination of the devices 100 and 200 allows a medical practitioner to change the look of his or her stethoscope whenever they want and reuse the devices 100 and 200 for the life of said devices. In a snap fit or screw together embodiment, the devices 100 and 200 can be taken off and a new set of devices placed on the tubing 10 similar to identical to as shown in FIGS. 4B and 4C, but with a different look or design.

Figure 5:
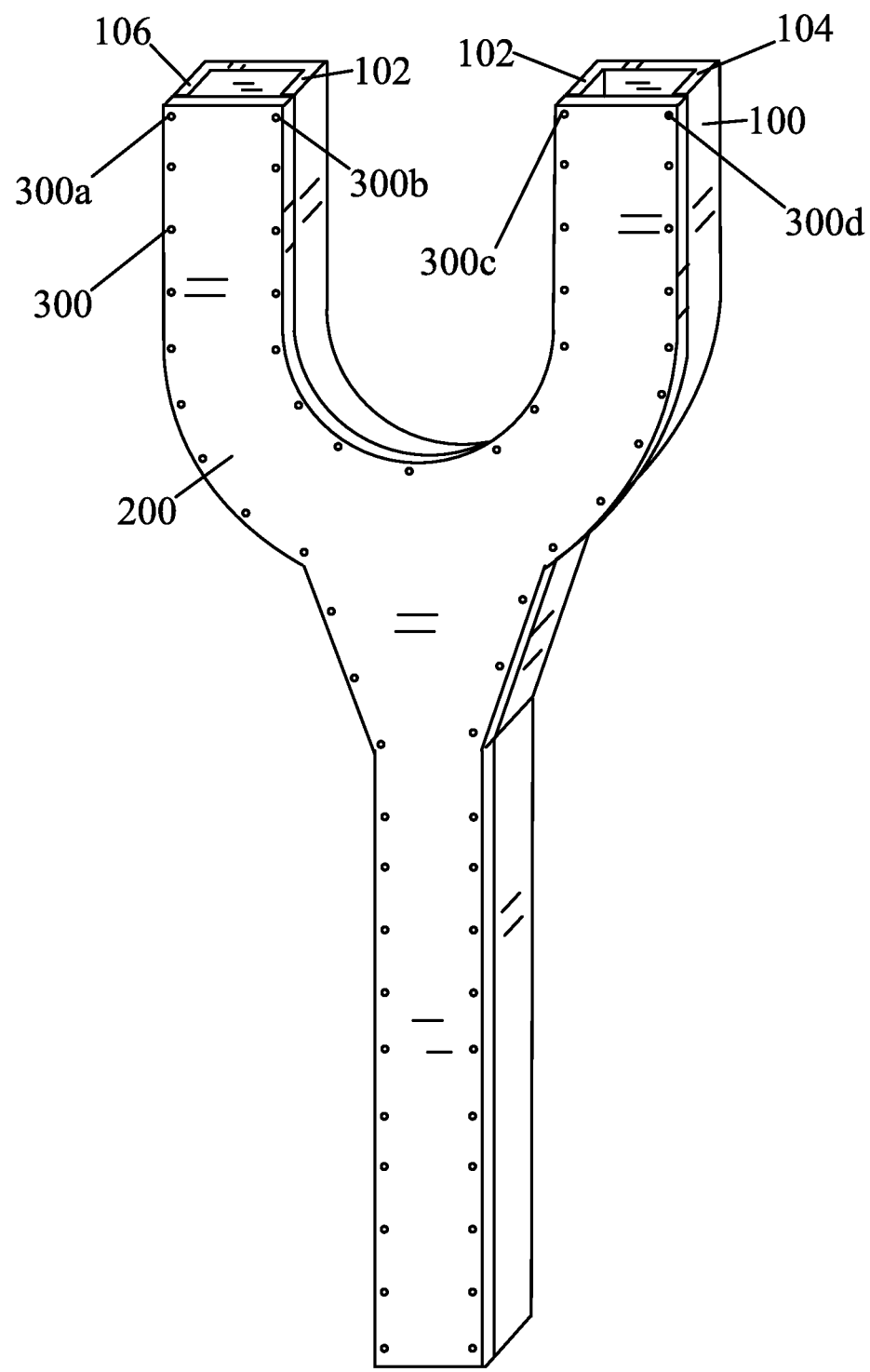
FIG. 5 shows a front, right, top perspective view of the first device of FIG. 2A, the second device of FIG. 3A, with the first device, the second device, with the first device and the second device shown assembled together.

FIG. 5 shows a front, right, top perspective view of the first device 100 of FIG. 2A, and the second device 200 of FIG. 3A, with the first device 100, and the second device 200 shown assembled together. The first device 100 may be attached to the second device 200 by screws, pins, or other fasteners 300 shown by FIG. 5. For example a plurality of fasteners or pins 300a of 300 may connect the second device 200 to the wall 106 of the first device 100, a plurality of fasteners or pins 300b may connect the second device 200 to the wall 102 of the first device 100, a plurality of fasteners or pins 300c may connect the second device 200 to the wall 102, and a plurality of fasteners or pins 300d may connect the second device 200 to the wall 104 in order to connect the first device 100 and the second device 200. The first device 100 and the second device 200 may be connected in the manner shown in FIG. 5 or some other manner, when a portion or preferably all of the stethoscope tubing 10, is in the position in between the devices 100 and 200 as shown in FIGS. 4B and 4C.

Figure 6:
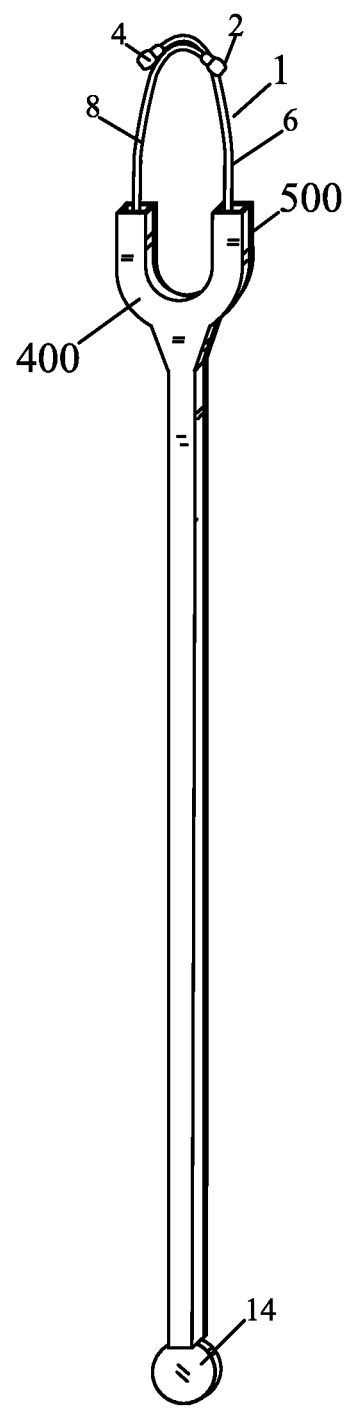
FIG. 6 shows a front, right, top perspective view of another device in accordance with another embodiment of the present invention, wherein all, or nearly all of stethoscope tubing is covered.

FIG. 6 shows a front, right, top perspective view of a device 400 and a device 500 in accordance with another embodiment of the present invention, wherein all, or nearly all of stethoscope tubing 10 is covered. The devices 400 and 500 may be identical to the devices 100 and 200, respectively, except that they are sized and configured to cover the entire stethoscope tubing 10 and in one or more embodiments connector 12, up to diaphragm or chest piece 14. The devices 400 and 500 may be connected together in a manner similar to or identical to devices 100 and 200.

The devices 100 and 200 or 400 and 500 may be configured for different types of stethoscopes. They may have different designs, lengths, and sizes depending on the type of stethoscopes. Such different designs, lengths and sizes are within the scope of the present invention.

Figure 7:
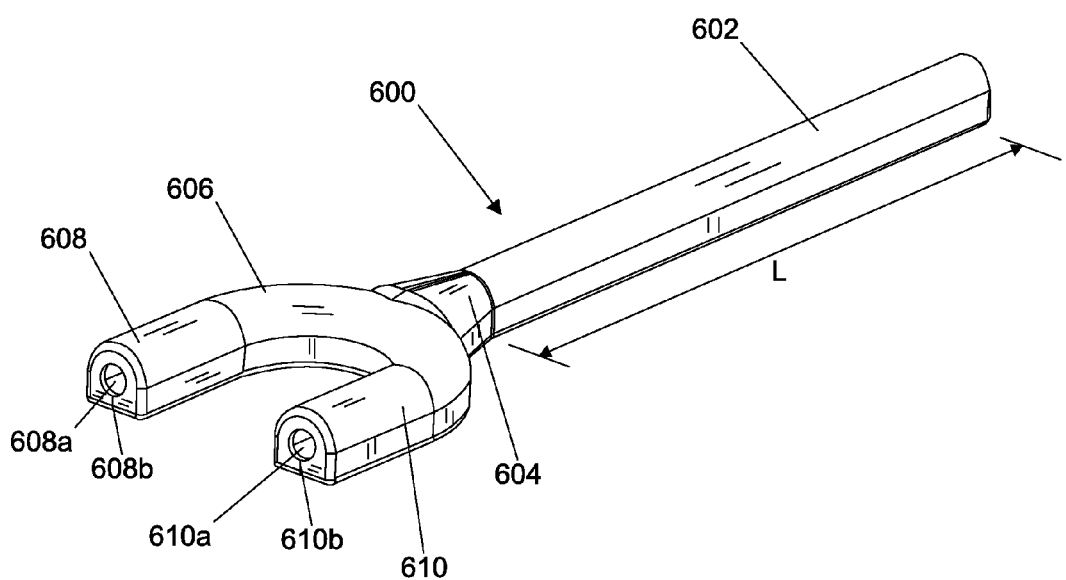
FIG. 7 shows a front, top and right side perspective view of an apparatus in accordance with another embodiment of the present invention.
Figure 8:
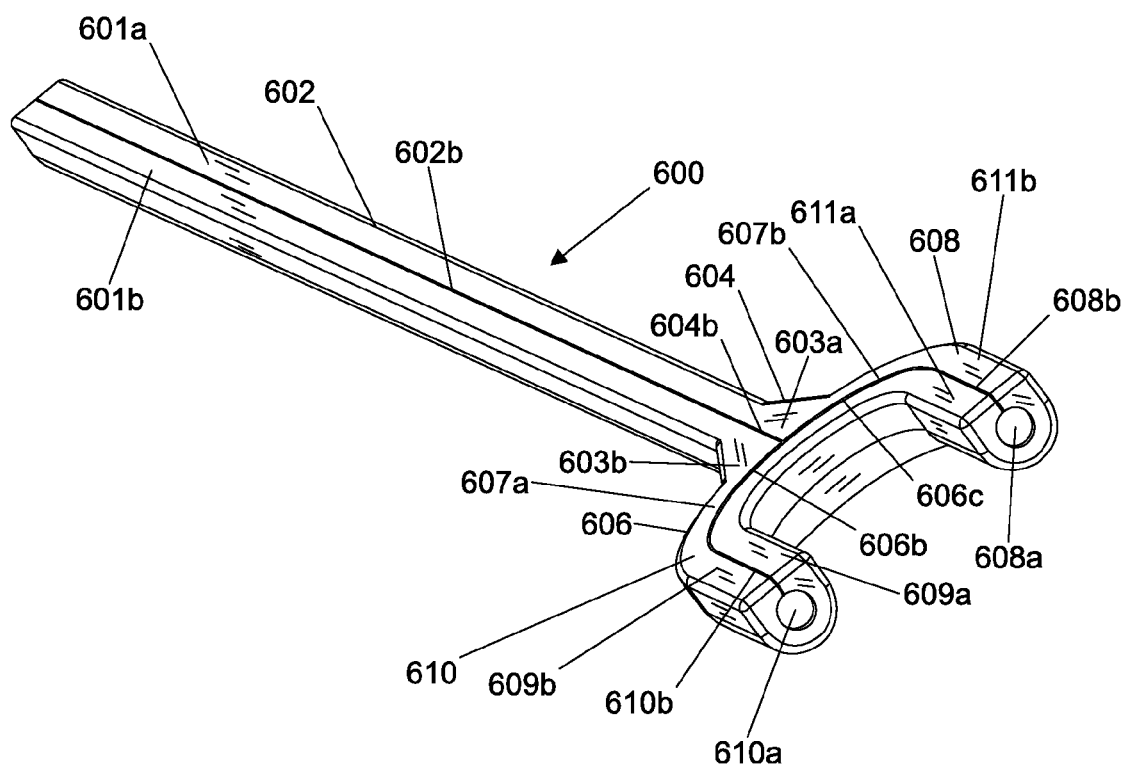
FIG. 8 shows a front, bottom, and right side perspective view of the apparatus of FIG. 7.
Figure 9:
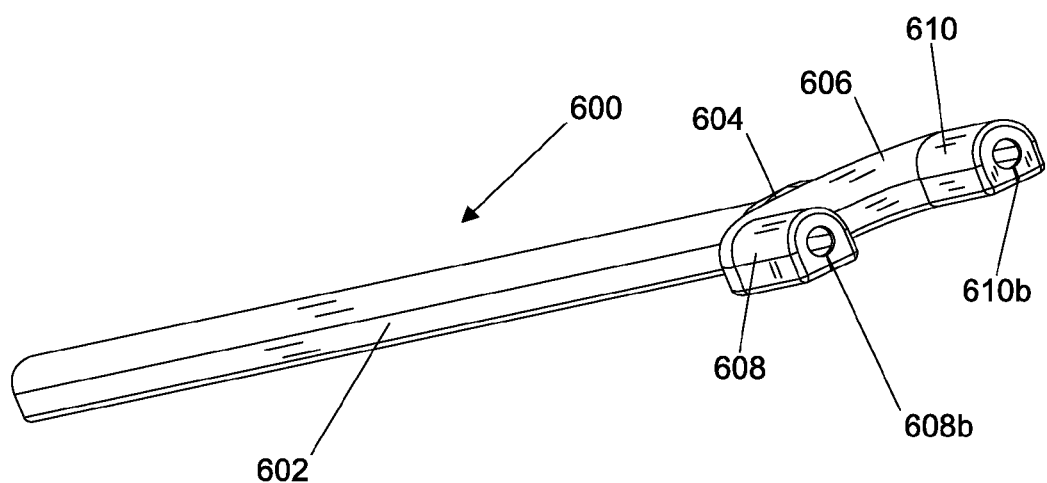
FIG. 9 shows a front, top, and left side perspective view of the apparatus of FIG. 7.
Figure 10:
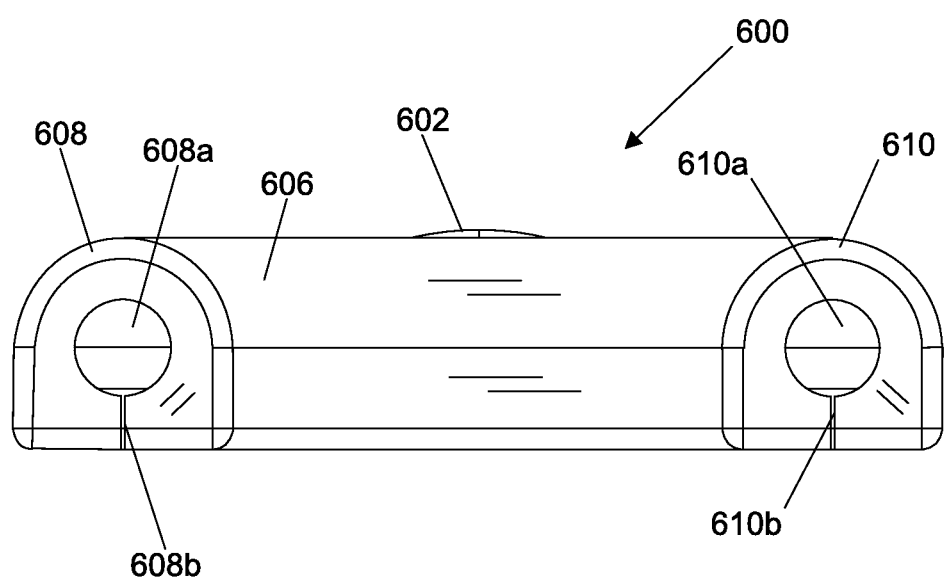
FIG. 10 shows a front view of the apparatus of FIG. 7.
Figure 11:
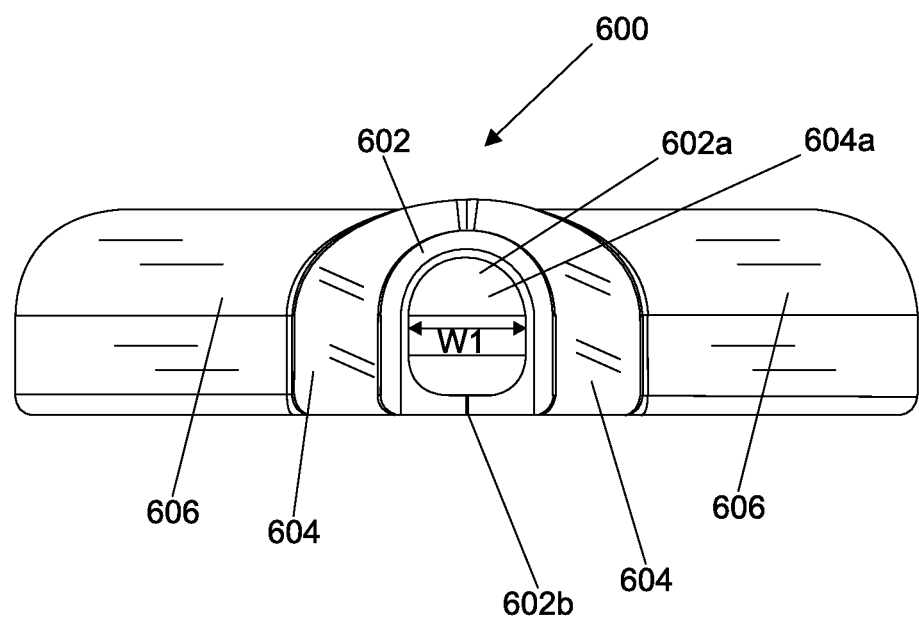
FIG. 11 shows a rear view of the apparatus of FIG. 7.

FIG. 7 shows a front, top and right side perspective view of an apparatus 600 in accordance with another embodiment of the present invention. FIG. 8 shows a front, bottom, and right side perspective view of the apparatus 600. FIG. 9 shows a front, top, and left side perspective view of the apparatus 600. FIG. 10 shows a front view of the apparatus 600. FIG. 11 shows a rear view of the apparatus 600.

Referring to FIGS. 7-11, the apparatus 600 includes a sections 602, 604, 606, 608, and 610. The section 602 is elongated. The section 604 is tapered. The section 606 is U-shaped. The sections 608 and 610 are substantially straight.

The section 602 has an opening or bore 602a running the length, L, of the section 602, as shown by FIGS. 7 and 11. The opening 602a has a width W1 which is typically less than a diameter, D1 of a diaphragm device 14 of the stethoscope 1 as shown by FIG. 12B. The section 602 also has a slit 602b running its entire length L, as shown in FIG. 8. The slit 602b when opened leads to the bore 602a.

The section 604 has an opening or bore 604a which is integrated or joined with the opening or bore 602a. The section 604 also has a slit 604b which when opened leads to the bore 604a, and which is connected to or is integrated with the slit 602b.

The section 606 is U-shaped. The section 606 has a branch 607a which has a bore, not shown which joins or is integrated with the bore 604a. The section 606 also has a branch 607b which has a bore, not shown, which is integrated with bore 604a. The section 606 has slits 606b and 606c which are connected to slit 604b. The slits 606b and 606c, when opened lead to the bores in section 606 which connected to bore 604b and 602b.

The section 608 includes an opening or bore 608a and a slit 608b which connect to a bore in portion 606c of section 606, and a slit 607b of section 606, respectively. The section 610 includes an opening or bore 610a and a slit 610b which connect to a bore in portion 606b of section 606, and a slit 607a of section 606, respectively.

Figure 12A:
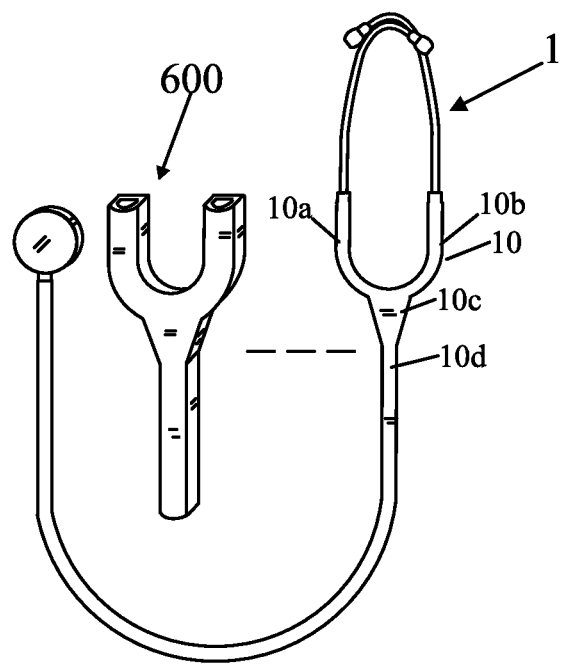
FIG. 12A shows a front, right, top perspective view of the device of FIG. 7, and the stethoscope of FIG. 1, with the device of FIG. 7, and the stethoscope of FIG. 1 shown apart from each other.
Figure 12B:
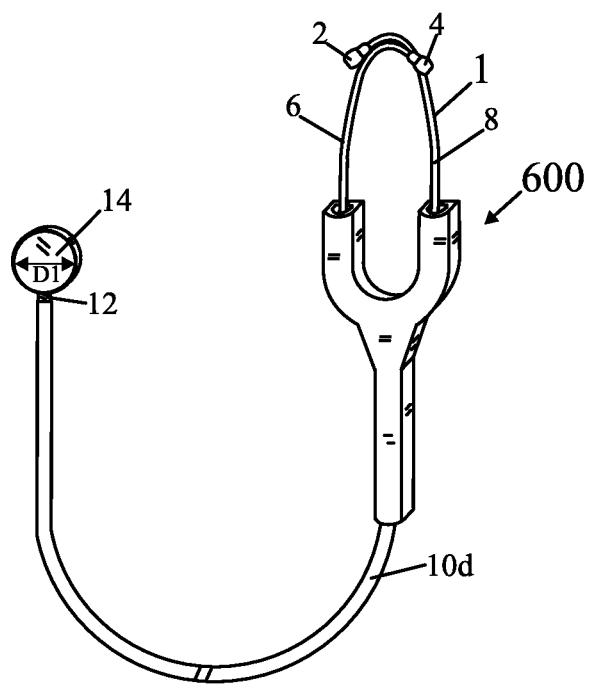
FIG. 12B shows a front, right, top perspective view of the device of FIG. 7, and the stethoscope of FIG. 1, with the device of FIG. 7, and the stethoscope of FIG. 1 shown assembled together.

In operation, the apparatus 600 can be attached to the stethoscope 1 as shown by FIGS. 12A and 12B. Referring to FIG. 8, in order to attach the apparatus 600, the slits 602b, 604b, 607a, 607b, 610b, and 608b are opened up. For example, part 601a and 601b of section 602 may be spread apart or flexed apart from each other to open up slit 602b. Similarly, part 603a and 603b of section 604 may be spread apart or flexed apart from each other to open up slit 604b. Similarly, part 609a and 609b of section 610 may be spread apart or flexed apart from each other to open up slit 610b. Similarly, part 611a and 611b of section 608 may be spread apart or flexed apart from each other to open up slit 608b.

With the slits 602b, 604b, 606b, 606c, 610b, and 608b flexed opened, the portions 10a, 10b, junction portion 10c, and part of portion 10d of tubing 10 of the stethoscope 1 can be inserted through the appropriate slits into the appropriate bores of the apparatus 600. For example, at least part of tube portion 10a is inserted through slit 610b into bore or opening 610a, at least part of tube portion 10b is inserted through slit 608b into bore or opening 608b, at least part of junction portion 10c is inserted through slit 606b and 606c into a bore or opening of section 606, not shown, and at least part of portion 10d is inserted through slits 604b and 602b into bores 604a and 602a of the apparatus 600. After the appropriate part of the tubing 10 is inserted into the appropriate bore of the apparatus 600, the slits retract and close to the state shown in FIG. 8 or close to this state, to maintain a tight fit onto part of the tubing 10.

Although the invention has been described by reference to particular illustrative embodiments thereof, many changes and modifications of the invention may become apparent to those skilled in the art without departing from the spirit and scope of the invention. It is therefore intended to include within this patent all such changes and modifications as may reasonably and properly be included within the scope of the present invention's contribution to the art.

I claim:

1. An apparatus comprising:
   a stethoscope including
      a first ear tip device,
      a first portion of tubing,
      a second ear tip device,
      a second portion of tubing,
      a third portion of tubing,
      a junction portion of tubing, and
      a diaphragm device;
   wherein the first ear tip device is connected to the first portion of tubing, the second ear tip device is connected to the second portion of tubing, the junction portion of tubing connects the first portion of tubing, the second portion of tubing, and the third portion of tubing, and the third portion of tubing is connected to the diaphragm device;
   wherein the diaphragm device has an outer diameter; and
   further comprising a covering device for covering at least part of the first, the second, and the third portions of tubing, and the junction portion of tubing;
   wherein the covering device has first, second, and third bores in which the first, second, and third portions of tubing, respectively, of the stethoscope are located when the covering device is attached to the stethoscope in a first state;
   wherein each of the first, second, and third bores has a length and a width, wherein the length of each of the first, second, and third bores is greater than its width, and wherein the width of each of the first, second and third bores is less than the outer diameter of the diaphragm device;
   wherein the first, second, and third portions of tubing of the stethoscope are substantially parallel to the lengths of the first, second, and third bores, respectively, when the covering device is attached to the stethoscope in the first state;
   wherein the covering device is made of a flexible and elastic material;
   wherein the covering device has a first, second, and third slits, each of which can be pried open to allow the first, second, and third portions of tubing to be inserted into the first, second, and third bores of the covering device, respectively,
   and wherein the covering device has a water proof outer shell.

2. The apparatus of claim 1 wherein
   the water proof outer shell of the covering device is made of polyurethane.

3. The apparatus of claim 1 wherein
   the covering device has a U-shaped portion, and a straight portion connected to a bottom of the U-shaped portion.

4. The apparatus of claim 1 wherein
   the covering device is configured so that the first, second, and third slits close after the first, second, and third portions or tubing, are inserted into the first, second, and third bores.

5. An apparatus comprising
   a covering device for covering at least part of first, second, and third portions of tubing, and a junction portion of tubing of a stethoscope, the stethoscope including a diaphragm device connected to the third portion of tubing of the stethoscope;
   wherein the covering device has first, second, and third bores configured to receive first, second, and third portions of tubing, respectively, of the stethoscope when the covering device is attached to the stethoscope in a first state;
   wherein each of the first, second, and third bores has a length and a width, wherein the length of each of the first, second, and third bores is greater than its width, and wherein the width of each of the first, second and third bores is less than an outer diameter of the diaphragm device of the stethoscope;
   wherein the first, second, and third portions of tubing of the stethoscope are substantially parallel to the lengths of the first, second, and third bores, respectively, when the covering device is attached to the stethoscope in the first state;
   wherein the covering device has a first, second, and third slits, each of which can be pried open to allow the first, second, and third portions of tubing to be inserted into the first, second, and third bores of the covering device, respectively,
   and wherein the covering device has a water proof outer shell.

6. The apparatus of claim 5 wherein
   the water proof outer shell of the covering device is made of polyurethane.

7. The apparatus of claim 5 wherein
   the covering device has a U-shaped portion, and a straight portion connected to a bottom of the U-shaped portion.

8. The apparatus of claim 5 wherein
the covering device is configured so that the first, second, and third slits close after the first, second, and third portions or tubing, are inserted into the first, second, and third bores.

9. A method comprising
covering stethoscope tubing, including at least a first, second, third, and junction portions of tubing of a stethoscope with a covering device by attaching the covering device to the stethoscope in a first state;
wherein the stethoscope is comprised of:
  a first ear tip device,
  the first portion of tubing,
  a second ear tip device,
  the second portion of tubing,
  the third portion of tubing,
  the junction portion of tubing, and
  a diaphragm device;
wherein the first ear tip device is connected to the first portion of tubing, the second ear tip device is connected to the second portion of tubing, the junction portion of tubing connects the first portion of tubing, the second portion of tubing, and the third portion of tubing, and the third portion of tubing is connected to the diaphragm device;
wherein the diaphragm device has an outer diameter;
and wherein the covering device has first, second, and third bores in which the first, second, and third portions of tubing, respectively, of the stethoscope are located when the covering device is attached to the stethoscope in the first state;
wherein each of the first, the second, and the third bores has a length and a width, wherein the length of each of the first, the second, and the third bores is greater than its width, and wherein the width of each of the first, the second and the third bores is less than the outer diameter of the diaphragm device;
wherein the first, the second, and the third portions of tubing of the stethoscope are substantially parallel to the lengths of the first, the second, and the third bores, respectively, when the covering device is attached to the stethoscope in the first state;
wherein the covering device has a first, second, and third slits, each of which can be pried open to allow the first, second, and third portions of tubing to be inserted into the first, second, and third bores of the covering device, respectively,
wherein the covering device is made of a flexible and elastic material;
and wherein the covering device has a water proof outer shell.

10. The method of claim 9 wherein
the step of covering stethoscope tubing of the stethoscope includes covering all stethoscope tubing of the stethoscope.

11. The method of claim 9 wherein
the water proof outer shell of the covering device is made of polyurethane.

12. The method of claim 9 wherein
the covering device has a U-shaped portion, and a straight portion connected to a bottom of the U-shaped portion.

13. The method of claim 9 wherein
the covering device is configured so that the first, second, and third slits close after the first, second, and third portions or tubing, are inserted into the first, second, and third bores, respectively.

14. The apparatus of claim 1 wherein
the water proof outer shell of the covering device is made of silicone.

15. The apparatus of claim 1 wherein
the water proof outer shell of the covering device is made of a flexible water proof covering.

\* \* \* \* \*